United States Patent [19]

Lekholm et al.

[11] Patent Number: 4,730,618

[45] Date of Patent: Mar. 15, 1988

[54] CARDIAC PACER FOR PACING A HUMAN HEART AND PACING METHOD

[75] Inventors: Anders Lekholm; David C. Amundson, both of Bromma, Sweden

[73] Assignee: Siemens Aktiengesellschaft, Berlin and Munich, Fed. Rep. of Germany

[21] Appl. No.: 874,585

[22] Filed: Jun. 16, 1986

[51] Int. Cl.$^4$ .............................................. A61N 1/36
[52] U.S. Cl. .............................. 128/419 PG; 128/697; 128/723; 128/902
[58] Field of Search .......... 128/419 PG, 902, 419 PT, 128/723, 635, 697

[56] References Cited

U.S. PATENT DOCUMENTS

| | | |
|---|---|---|
| 3,593,718 | 7/1971 | Krusner et al. |
| 4,303,075 | 12/1981 | Heilman et al. ............... 128/419 PG |
| 4,428,378 | 1/1984 | Anderson et al. ............ 128/419 PG |
| 4,537,201 | 8/1985 | Delle-Vedove et al. ........... 128/697 |
| 4,543,955 | 10/1985 | Schroeppel ........................ 128/635 |
| 4,567,892 | 2/1986 | Plicchi et al. ................ 128/419 PG |
| 4,576,183 | 3/1986 | Plicchi et al. ........................ 128/723 |
| 4,596,251 | 6/1986 | Plicchi et al. ................ 128/419 PG |
| 4,614,192 | 9/1986 | Imran et al. ................... 128/419 PG |

FOREIGN PATENT DOCUMENTS 0089014 9/1983 European Pat. Off. .

Primary Examiner—William E. Kamm
Assistant Examiner—Timothy Keegan
Attorney, Agent, or Firm—Hill, Van Santen, Steadman & Simpson

[57] ABSTRACT

A cardiac pacer which generates pacing pulses at a predetermined pacing rate includes a device for making a body activity measurement. The measured body activity signal is non-linearly amplified such that signal portions having higher amplitudes are more amplified than signal portions having lower amplitudes. The non-linearly amplified body activity signal is integrated over a period of time. The predetermined pacing rate is varied dependent on the integrated signal.

10 Claims, 5 Drawing Figures

CARDIAC PACER FOR PACING A HUMAN HEART AND PACING METHOD

BACKGROUND OF THE INVENTION

1. Field of the Invention

This invention relates to a cardiac pacer for pacing a heart, in particular a human heart, wherein the pacing rate is controlled by body activity, for example respiration.

2. Related Applications:

The subject matter of the present application is related to the subject matter of the following co-pending applications filed simultaneously herewith: "A Cardiac Pacer For Pacing A Human Heart," Amundson, Ser. No. 874,588; "A Cardiac Pacer For Pacing A Heart," Elmqvist, Lekholm, Hedberg and Amundson, Ser. No. 874,597; "A Cardiac Pacer For Pacing A Heart," Lekholm and Amundson, Ser. No. 874,596; and "A Cardiac Pacer For Pacing A Human Heart," Lekholm and Amundson, Ser. No. 874,591.

The European Patent Application No. 0,089,014 describes a cardiac pacer where the signal received from an impedance measurement is compared with two threshold levels. Signal portions which lie outside the width of the two threshold levels are discarded from further signal processing since they are considered as impedance variations which do not have a certain consistency and therefore cannot contribute to possible evolution of a respiratory act. Only those portions which lie inside the width of the two threshold levels are further utilized for evaluation.

SUMMARY OF THE INVENTION

Objects

It is an object of the invention to provide for an improved cardiac pacer which allows for a simpler signal processing procedure for obtaining a body activity signal for controlling the pacer rate.

SUMMARY

According to this invention an improved cardiac pacer is provided which comprises (a) means for generating pacing pulses at a predetermined pacing rate;

(b) means for transmitting the pacing pulses to the heart for pacing;

(c) means for realizing a body activity measurement;

(d) means for obtaining a body activity signal depending on the body activity measurement, said signal varying according to the body activity level;

(e) means for non-linearly amplifying the body activity signal in a manner that signal portions having higher amplitudes are more amplified than signal portions having lower amplitudes;

(f) means for integrating the non-linearly amplified body activity signal over a period of time; and (g) means for varying the predetermined pacing rate dependent on the energy signal.

By non-linearly amplifying and integrating the body activity signal low amplitude and/or high-frequency noise are automatically eliminated. A threshold evaluation is no longer necessary.

In a preferred embodiment the means for non-linearly amplifying the body activity signal comprising means for squaring the body activity signal.

In another preferred embodiment the body activity signal is a respiratory signal. It can however also be a signal obtained from a body accelerometer, core temperature sensor, pH sensor, $pO_2$ sensor etc.

The foregoing and other objects, features and advantages of the invention will be apparent from the following more particular description of a preferred embodiment of the invention, as illustrated in the accompanying drawings.

DESCRIPTION OF THE PREFERRED EMBODIMENT

Figure 1:
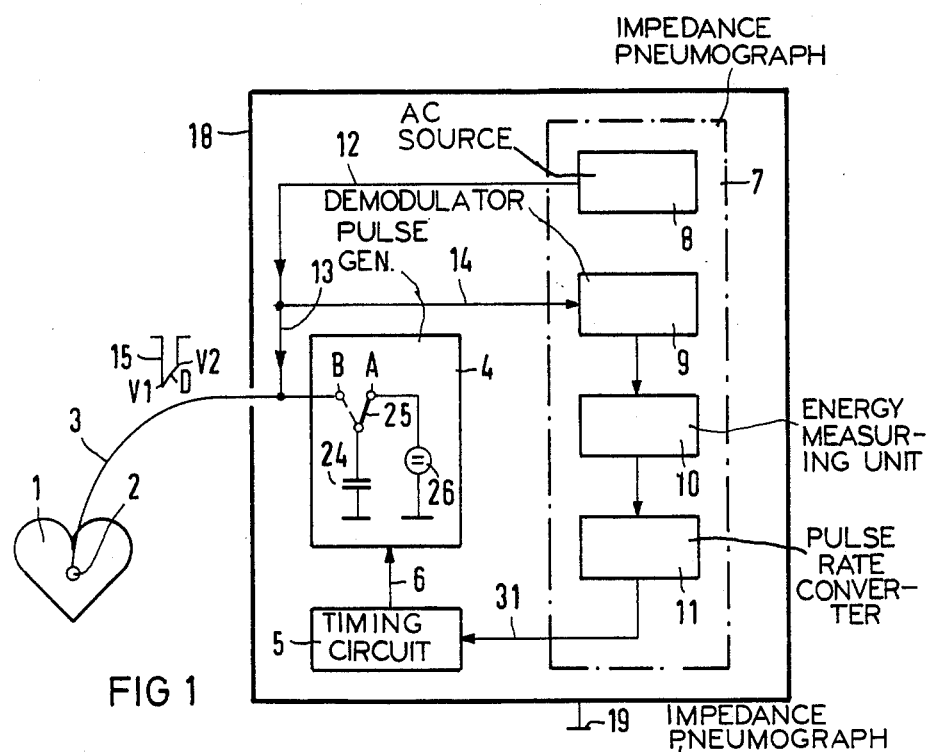
FIG. 1 shows a first embodiment of a cardiac pacer comprising the invention in a schematic block diagram.
Figure 2:
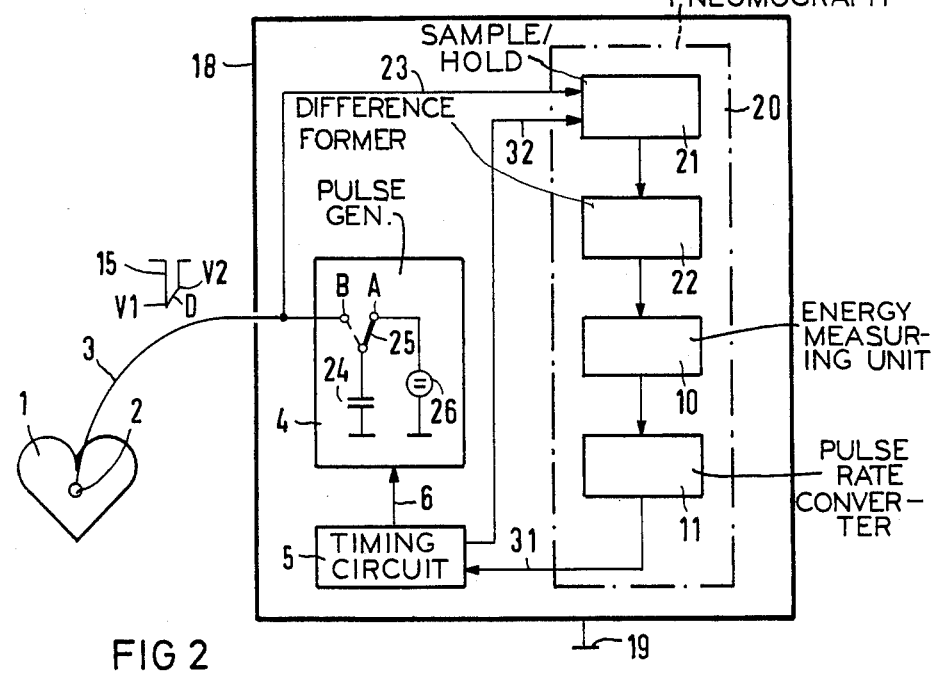
FIG. 2 shows a second embodiment of a cardiac pacer comprising the invention in a schematic block diagram.

In FIGS. 1 and 2 a human heart which has to be paced is generally designated with 1. A pacing electrode 2 is inserted in the human heart 1 in a manner and position that the heart can most efficiently be paced. The pacing electrode 2 is connected through a pacing lead 3 with a pacing pulse generator 4. A timing circuit 5 controls the pacing rate of the pacing pulse generator 4 through line 6.

Figure 5:
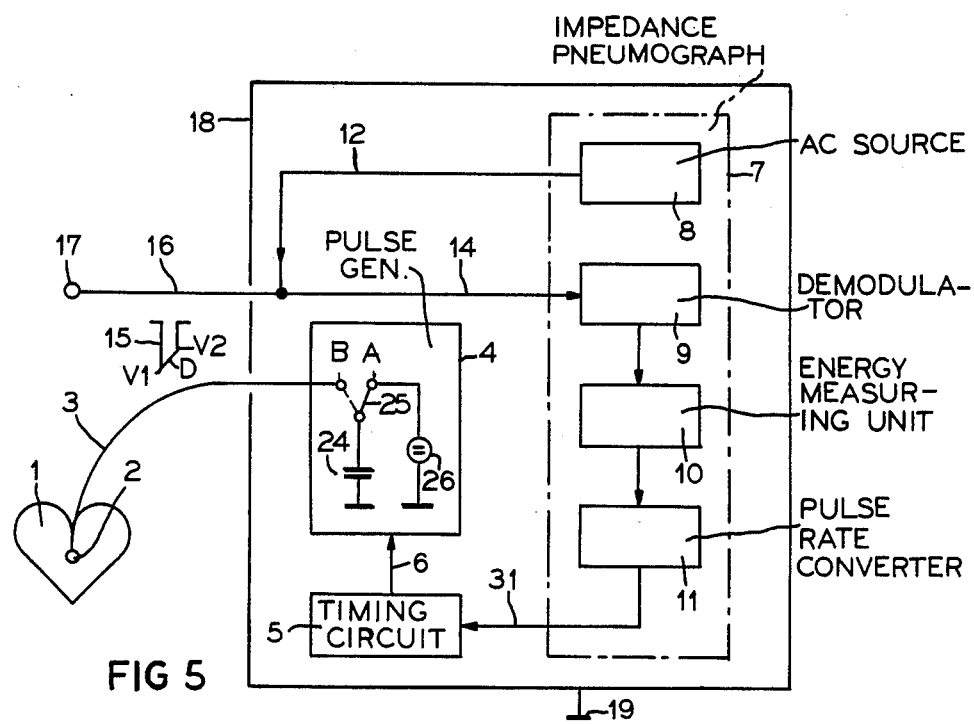
FIG. 5 shows another embodiment of a cardiac pacemaker as shown in FIG. 1 in a schematic block diagram.

According to FIG. 1 an impedance pneumograph 7 comprises an AC source 8 for generating a continuous alternating current, a demodulator 9, an energy measuring unit 10 in accordance with the principles of the invention and a voltage to pulse rate converter 11. The AC source 8 is connected with the pacing lead 3 by lines 12 and 13. The demodulator 9 is connected with the pacing lead 3 by lines 13 and 14. Under the circumstances the current of the AC source 8 is supplied to the pacing electrode 2 together with the pacing pulses 15. Nevertheless this embodiment can be modified in a manner as shown in FIG. 5 wherein instead of utilizing the pacing electrode 2, a separate electrode is provided for impedance measurement. In this case the AC source 8 and the demodulator 9 are connected through an additional lead 16 with a separate impedance measuring electrode 17. In both cases the output signal (body activity signal) of the demodulator 9 is a measure of breathing rate and tidal volume.

In FIG. 1 the pacing pulse generator 4, the timing circuit 5 and the impedance pneumograph 7 are all encapsuled in an implantable conductive (metallic) housing 18 which is the housing of the cardiac pacer. The metallic housing 18 defines both the passive electrode for pacing and the second electrode for impedance measurement as indicated in FIG. 1 with reference numeral 19.

In FIG. 2 an impedance pneumograph 20 includes a sample and hold circuitry 21 and difference former 22 in addition to the energy measuring unit 10 and a voltage to pulse rate converter 11. The sample and hold circuitry 21 of the impedance pneumograph 20 is connected with the pacing lead 3 of the pacing pulse generator 4 through line 23 for processing the pacing pulses 15 such that a respiratory signal is obtained from the pacing pulses 15 by evaluating the amplitude decays D of pacing pulses 15. The amplitude decay D changes according to alternating body impedance during respiration. The measurement may also be done by a division of voltage and current. Again the pacing pulse generator 4, the timing circuit 5 and the impedance pneumograph 20 are all encapsuled in an implantable conductive (metallic) housing 18 which is the housing of the cardiac pacer. The housing 18 again defines both the passive electrode for pacing and the second electrode for impedance measurement as indicated in FIG. 2 with reference numeral 19.

As illustrated in FIGS. 1 and 2 the pacing pulse generator 4 comprises an output capacitor 24 which is switchable by means of switch 25 between battery 26 (switch position A) and pacing lead 3 (switch position B). In switch position A and the output capacitor 24 is charged by the battery 26 to a voltage V1. In switch position B the output capacitor 24 is discharged through pacing lead 3 as pacing pulse 15.

In the embodiment of FIG. 2 the amount of discharge depends on the impedance variations of the patient's thorax during respiration. According to FIG. 2 the pacing pulse 15 discharges from V1 to V2 (amplitude decay D). The sample and hold circuitry 21 samples and holds the voltages V1 and V2 of output capacitor 24. The difference former 22 forms the differences V1−V2 which is again a measure for the breathing rate, i.e. a respiratory signal.

Figure 3:
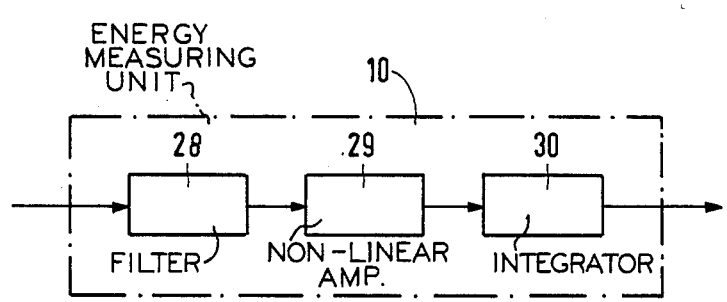
FIG. 3 shows an energy measuring device including the invention of an impedance pneumograph of the embodiments of FIGS. 1 and 2 in more detail.

In both embodiments each respiratory signal is supplied to the energy measuring device 10, which according to FIG. 3 comprises filter 28, a non-linear amplification (e.g. squaring) circuitry 29 and an integrator 30. The non-linear amplification circuitry 29 amplifies the filtered respiratory signal such that signal portions having higher amplitudes are more amplified than signal portions having lower amplitudes. Under these conditions signal including the respiration signal are enhanced with respect to low amplitude noise for further processing. Non-linear amplification circuits of this kind are well known in the art need not be described in more detail. The output signal of the non-linear amplification circuitry 29 is integrated in integrator 30 over a period of time, e.g. in the range of 5 to 30 s. By integrating, high-frequency noise is significantly reduced. The voltage to pulse rate converter 11 in FIGS. 1 and 2 converts the integrated signal into a pulse rate according to the breathing rate.

The voltage to pulse rate converter 11 controls the time base unit 5 through line 31 such that a predetermined (e.g. programmable) basic pacing rate of the pacing pulse generator 4 is varied dependent on the respiratory signal. In FIG. 2 the line 32 is a control line from the time base unit 5 to the sample and hold circuitry 21 of impedance pneumograph 20.

Figure 4:
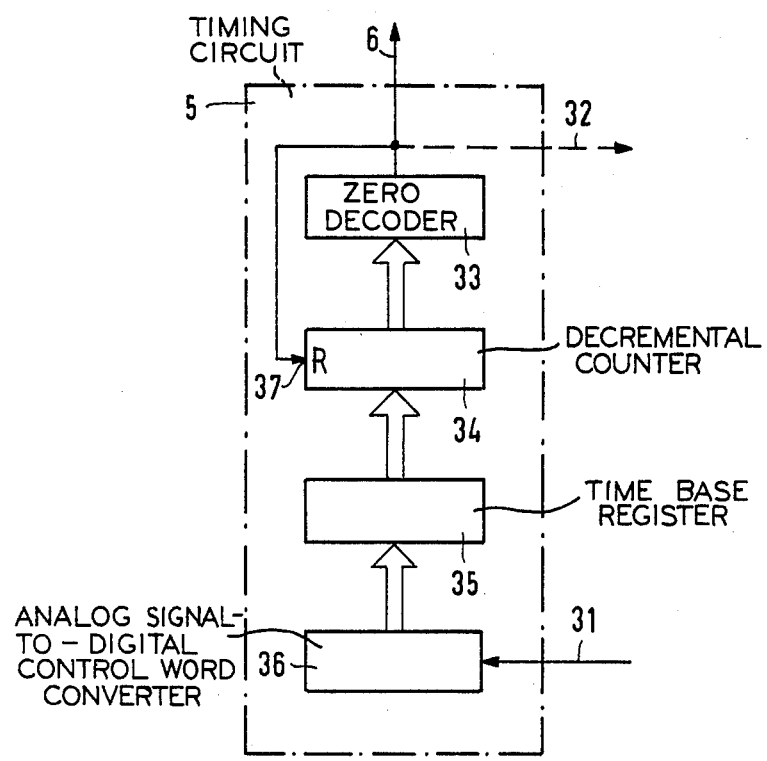
FIG. 4 the time base unit of the embodiment of FIGS. 1 and 2 in more detail.

According to FIG. 4 the time base unit 5 comprises a zero decoder 33, decremental counter 34, a time base register 35 and an analog signal to digital control word converter 36. The decremental counter 34 includes a reset input 37. The signal to digital control word converter 36 converts the analog pulse rate signal of the voltage to pulse rate converter 11 into a digital control word. This digital control word is supplied to the time base register 35. It controls the time base register 35 such that a basic pacing rate, e.g. 60 beats/min., is varied dependent on the respiration rate. When the breathing rate increases the time base register 35 increases the counting speed of down counter 34 so that it reaches zero faster than at basic rate. Under these conditions the zero decoder 33 generates switching signals at higher rates, so that the output capacitor 24 of the pacing pulse generator 4 charges and discharges at higher rates. As a result the pacing rate increases dependent on increasing breathing rate as desired.

Having thus described the invention with particular references to the preferred forms thereof, it will be obvious to those skilled in the art to which the invention pertains, after understanding the invention, that various changes and modifications may be made therein without departing from the spirit and scope of the invention as defined by the claims appended hereto. For example the impedance measurement electrodes do not need to be implanted. They can also be secured on the patient's chest, if desired. Such a possibility is for example illustrated in U.S. Pat. No. 3,593,718.

What is claimed is:

1. A cardiac pacer for pacing a human heart in a patient comprising
    (a) means for generating pacing pulses at a predetermined pacing rate;
    (b) means for transmitting the pacing pulses to the heart for pacing;
    (c) means for making a body activity measurement of the patient;
    (d) means for obtaining a body activity signal depending on the body activity measurement, said signal varying according to the body activity level;
    (e) means for non-linearly amplifying all of the body activity signal such that signal portions having higher amplitudes are more amplified than signal portions having lower amplitudes;
    (f) means for integrating the non-linearly amplified body activity signal over a period of time; and
    (g) means for varying the predetermined pacing rate dependent on the integrated signal.

2. A cardiac pacer as claimed in claim 1, wherein said means for non-linearly amplifying the body activity signal is means for squaring the body activity signal.

3. A cardiac pacer as claimed in claim 1, wherein said integrated means integrates said body activity signal over a time period in the range of 5 to 30s.

4. A cardiac paceer as claimed in claim 1, wherein said means for obtaining a body activity signal is a means for obtaining a respiratory signal.

5. A cardiac pacer as claimed in claim 4, wherein said means for making a body activity measurement means for making a body impedance measurement.

6. A method for pacing a heart in a patient comprising the steps of:
    generating pacing pulses at a predetermined pacing rate;
    transmitting said pacing pulses to said heart for pacing thereof;
    making a measurement of selected body activity of said patient;
    generating a body activity signal in dependence upon said body activity measurement, said body activity signal varying according to the level of body activity of said patient;
    non-linearly amplifying all of said body activity signal by more greatly amplifying portions of said body activity signal having higher amplitudes than portions of said signal having lower amplitudes;
    integrating the non-linearly amplified body activity signal over a selected period of time; and varying said predetermined pacing rate in dependence on said integrated signal.

7. A method as claimed in claim 6, wherein the step of non-linearly amplifying said body activity signal is further defined by squaring said body activity signal.

8. A method as claimed in claim 6, wherein the step of integrating the non-linearly amplified body activity signal is further defined by integrating said non-linearly amplified body activity signal for a period in the range of 5 to 30s.

9. A method as claimed in claim 6, wherein the step of making a measurement of the body activity of the patient is further defined by making a measurement of the respiratory activity of said patient.

10. A method as claimed in claim 9, wherein the step of making a respiratory activity measurement of said patient is further defined by making a body impedance measurement of said patient.

* * * * *